US00PP11241P

United States Patent [19]

Walden

[11] Patent Number: Plant 11,241

[45] Date of Patent: Feb. 22, 2000

[54] FLORIBUNDA ROSE PLANT NAMED 'JACMEGIP'

[75] Inventor: John K. Walden, Thousand Oaks, Calif.

[73] Assignee: Bear Creek Gardens, Inc., Medford, Oreg.

[21] Appl. No.: 09/081,880

[22] Filed: May 19, 1998

[51] Int. Cl.[7] ..... A01A 5/00

[52] U.S. Cl. ..... Plt./148

[58] Field of Search ..... Plt./148, 128

[56] References Cited

U.S. PATENT DOCUMENTS

| | | | |
|---|---|---|---|
| P.P. 5,246 | 6/1984 | Warriner | Plt./127 |
| P.P. 5,770 | 7/1986 | de Ruiter | Plt./122 |

*Primary Examiner*—Howard J. Locker

*Attorney, Agent, or Firm*—Klarquist Sparkman Campbell Leigh & Whinston LLP

[57] ABSTRACT

Floribunda rose plant having long lasting flowers of a clear, light pink color; dark green, powdery mildew resistant foliage; well formed bud and flower; and vigorous upright growth habit.

1 Drawing Sheet

The present invention relates to a new and distinct variety of rose plant of the floribunda class which was originated by me by crossing two unnamed seedlings.

The primary object of this breeding was to produce a new rose variety having a large, light pink color flower, dark green, disease resistant foliage, an upright plant habit suitable for pot forcing in a greenhouse and grown and propagated from softwood cuttings. The objective was substantially achieved, along with other desirable improvements, as evidenced by the following unique combination of characteristics that are outstanding in the new variety and that distinguish it from its parents, as well as from all other varieties of which I am aware:

1. Clear, light pink flower color;
2. Dark green foliage;
3. Resistance to powdery mildew;
4. Well formed bud and flower;
5. Long lasting flowers; and
6. Vigorous, upright growth.

'JACmegip' produces in sixteen to eighteen weeks a quality pot rose when propagated from softwood to semi-hardwood cuttings and grown in a 5½ to 6 inch pot in a greenhouse.

Asexual reproduction of this new variety by softwood cuttings, as performed at Somis, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (JACibe, U.S. Plant Pat. No. 5,246×RUImired, U.S. Plant Pat. No. 5,770).

*Pollen parent.*—Unnamed seedling (unnamed seedling×unnamed seedling).

Classification:

*Botanical.*—Rosa hybrida.

*Commercial.*—Floridunda.

FLOWER

Observations made from specimens grown in a greenhouse environment at Somis, Calif., from September 1994 to April 1997.

Blooming habit: Recurrent.

Bud:

*Size.*—About ¾ inch long when the petals start to unfurl.

*Form.*—Short (¾ to 1"), pointed ovoid.

*Color.*—When sepals first divide, but color is near Red Group 56A. When half blown, the upper sides of the petals are near Red Group 56A, and the lower sides of the petals are near Red group 54C.

*Sepals.*—Color: Yellow-Green Group 146C. Surface texture: Smooth, glabrous. There are three lightly appendaged sepals. There are two unappendaged sepals with hairy edges.

*Receptacles.*—Color: Between Yellow-Green Groups 144A and 144B. Shape: Funnel. Size: Small (about ¼"×¼"). Surface: Smooth.

*Peduncle.*—Length: Short (about ⅛–1"). Surface: Smooth. Color: Yellow-Green Group 152C. Strength: Erect.

Bloom:

*Size.*—Medium. Average open diameter is about 2¾–3 inches.

*Borne.*—Singly and in clusters of three to five buds having a pyramidal shape.

*Stems.*—Short (about 8").

*Form.*—When first open: High centered. Permanence: Flattens, outer petals curl back.

*Petalage.*—Number of petals under normal conditions: 30–35.

*Color.*—The upper sides of the petals are near Red Group 56A. The reverse sides of the petals are near Red Group 56A. The base of each petal has a pale yellow (Yellow Group 10D) crescent, about ¼" in size. The major color on the upper sides is near Red Group 56A.

*Variegations.*—None.

*Discoloration.*—At the end of the first day: Near Red Group 56A. At the end of the third day: Near Red Group 56A.

*Fragrance.*—None.

Petals:

*Texture.*—Thick.

*Shape.*—Pointed; deltoid.

*Form.*—Edges slightly quilled.

*Arrangement.*—Imbricated (shingle-like). Petaloids in the center: Few (2 to 4), small; Color: Red Group 56A.

*Persistance.*—Petals drop off cleanly before drying.

*Lastingness.*—On the plant: Very long (14–16 days). As a cut flower: Not tested.

Reproductive parts:

*Anthers.*—Size: Medium. Quantity: Many. Color: Yellow Group 13B. Arrangement: Regular around styles.

*Filaments.*—Color: Yellow-green.

*Pollen.*—Color: Gold-yellow.

*Styles.*—Color: Yellow Group 2D.

*Stigmas.*—Color: Yellow Group 2C.

Plant:

*Form.*—Bush.

*Growth.*—Vigorous; upright. At maturity in a garden environment, height is 24–30 inches, width is 24 inches.

Foliage: Number of leaflets on normal mid-stem leaves: Five, occasionally seven.

*Size.*—5 inches long×2¾ inches wide.

*Quantity.*—Normal.

*Color.*—New foliage: Upper side: Yellow-Green Group 146A. Lower side: Greyed-Purple Group 184A. Old foliage: Upper side: Green Group 137A. Lower side: Near Green Group 137C.

Leaflets:

*Shape.*—Pointed oval.

*Texture.*—Glossy.

*Edge.*—Serrated.

*Serration.*—Single.

*Petiole rachis.*—Color: Reddish.

*Petiole underside.*—Smooth, occasionally with prickles.

*Stipules.*—Long (13/16"), serrated.

*Disease resistance.*—Resistant to mildew under normal growing conditions at Somis, Calif.

Wood:

*New wood.*—Color: Greyed-Purple Group 185A rapidly turning green. Bark: Smooth.

*Old wood.*—Color: Green Group 137C. Bark: Smooth.

Prickles:

*Quanity.*—On main canes from base: Ordinary. On laterals from main canes: Ordinary.

*Form.*—Short, straight to slightly hooked downward.

*Color when young.*—Underlying light green color with a reddish overlay.

*Color when mature.*—Greyed-Orange 165B.

Small prickles:

*Quantity.*—On main stalks: None. On laterals: None.

I claim:

1. A new and distinct variety of rose plant of the floribunda class, as herein shown and described, characterized particularly by its long lasting flowers of a clear, light pink color; dark green, powdery mildew resistant foliage; well formed bud and flower; and vigorous upright growth habit.

* * * * *

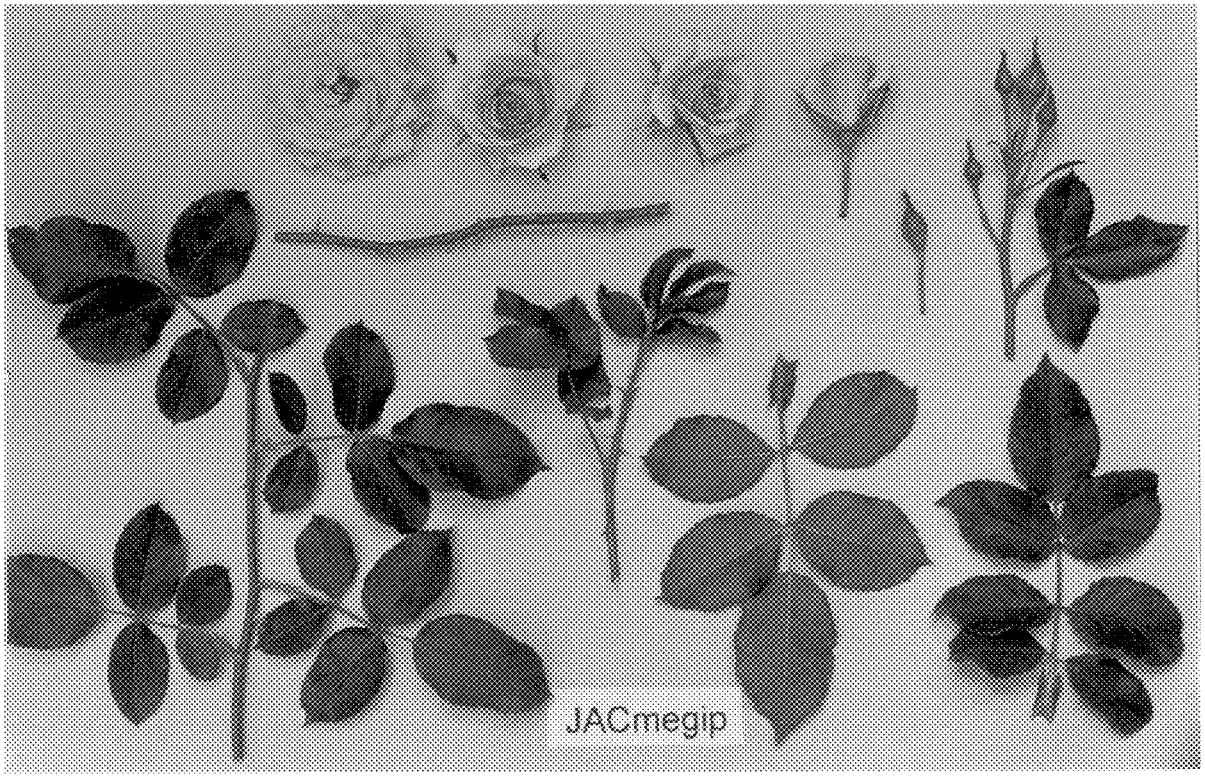
JACmegip

UNITED STATES PATENT AND TRADEMARK OFFICE

CERTIFICATE OF CORRECTION

PATENT NO. : PP11,241
DATED : February 22, 2000
INVENTOR(S) : John K. Walden

It is certified that error appears in the above-identified patent and that said Letters Patent is hereby corrected as shown below:

In the Specification:

Column 2,
Lines 28, reads "(about 1/8—1")". It should read --(about 7/8 - 1")--.

Signed and Sealed this

Third Day of July, 2001

*Attest:*

Nicholas P. Godici

*Attesting Officer*

NICHOLAS P. GODICI
*Acting Director of the United States Patent and Trademark Office*